United States Patent [19]

Pearce et al.

[11] Patent Number: 4,808,765

[45] Date of Patent: Feb. 28, 1989

[54] SULFUR REMOVAL FROM HYDROCARBONS

[75] Inventors: Roscoe L. Pearce, Cypress; Richard A. Wolcott, Angleton, both of Tex.

[73] Assignee: The Dow Chemical Company, Midland, Mich.

[21] Appl. No.: 74,841

[22] Filed: Jul. 17, 1987

[51] Int. Cl.⁴ .......................... C07C 7/11; C01B 31/26
[52] U.S. Cl. ...................................... 585/860; 208/206; 208/236; 208/240; 423/229; 423/245.1
[58] Field of Search .............. 208/193, 205, 206, 207, 208/236, 237, 240, 229; 585/860; 423/228, 243, 245

[56] References Cited

U.S. PATENT DOCUMENTS

| | | | |
|---|---|---|---|
| 2,311,342 | 2/1943 | Kerns et al. | 208/236 X |
| 2,547,181 | 4/1951 | Tom et al. | 208/205 |
| 2,560,374 | 7/1951 | Schmidl | 208/205 |
| 2,914,469 | 11/1959 | Anderson et al. | 208/236 |
| 3,098,705 | 7/1963 | Bally | 208/236 X |
| 3,829,521 | 8/1974 | Green | 208/236 X |
| 3,856,921 | 12/1974 | Shrier et al. | 208/207 X |
| 4,233,141 | 11/1980 | Bearon et al. | 208/236 |

Primary Examiner—Glenn Caldarola
Attorney, Agent, or Firm—G. R. Baker

[57] ABSTRACT

There is disclosed a process for treating liquid (liquifiable) and gaseous hydrocarbons to remove substantially all of the acid gases including COS by contacting the hydrocarbon streams with specific aqueous treating agents in a series of sequential specific limit operations and apparatus.

13 Claims, 1 Drawing Sheet

SULFUR REMOVAL FROM HYDROCARBONS

BACKGROUND OF THE INVENTION

Natural gases and liquid (liquified) hydrocarbons are known to contain acid gases such as carbon dioxide and one or more sulfur containing components such as carbonyl sulfide, hydrogen sulfide, mercaptans and the like, many of which must be removed to make the hydrocarbons suitable for the many uses, such as polymerizations, combustion, and the like, because of the deleterious effect these gases have on catalysts, air quality, etc.

Carbonyl sulfide (COS) is contained in natural gas in small quantities i.e., 50–500 ppm and in liquid (liquified) hydrocarbon streams in concentrations in the 1–100 ppm range. The specification level in treated products is in the 1 ppm range or less for natural gas and most liquid streams. There are several processes available for removing COS to these levels. However, some specifications for liquid (liquified) hydrocarbon products are in the .50–1000 ppb range. For example, ethylene and propylene for polyethylene and polypropylene manufacture respectively, normally have a 50 or less ppb limit. There are no known techniques for removing COS to these low levels, e.g. ppb, which are commercially viable. The removal of carbonyl sulfide (COS) is very poor in caustic solutions. No more than 10–15% removal can be expected in conventional caustic solutions used in the conventional designed contactor.

There are, of course, several processes which employ physical solvents and or solvents which aid in the hydrolysis of COS to its component $CO_2$ and $H_2S$, but most of these processes have high make-up rates because the solvents and/or co-solvents are soluble in the liquid hydrocarbons to varying degrees requiring excessive make-up and thus are uneconomical in commercial processes.

In addition most of the materials for removing the COS to the ppm level usually form products which are either impure and command a very poor price or are objectionable from the environmental standpoint.

While mercaptans (RSH) are contained in some natural gases essentially all refinery liquid (liquified) hydrocarbon streams contain mercaptans. The specifications for refinery use and for polymerization reactions employing these products usually require the mercaptan level to be in the 1–20 ppm range.

The known art for the removal of mercaptans consists of one to three stages of contact with an aqueous caustic solution containing some type of solubilizer. Many patents have issued on this concept, most of which have expired. A separate unit is required for these operations. An example of one such process is the Merox Process requiring a separate unit in which the mercaptans are converted to their disulfides. The Merox solution is a caustic solution which contains a proprietary catalyst which is necessary for the economic conversion of RSH to RSSR. The art as practiced does not use unformulated or catalyst containing solution caustic for RSH removal since removal is poor in caustic alone, particularly with respect to removal of the higher molecular weight mercaptans, e.g., butyl and higher alkyl mercaptans.

The advantages and disadvantages of using monoethanolamine MEA in a refinery for removal of acid gases include some of the following:

Advantages

1. It has the capability of producing the lowest level of $H_2S$ and $CO_2$ in the product but has little or no selectivity required for tail gas sulfur producing processes.
2. It can be partially reclaimed in the event of thermal degradation or build-up of heat stable salts but often the high MEA usage rates result from these reclaiming operations (necessitated by the irreversible reaction of COS and MEA) as well as losses to the products because of MEA's solubility in the products.
3. It can hydrolyze COS and thus the product meets farily low COS specifications.

Disadvantages

1. It has high heats of reaction with $H_2S$ and $CO_2$.
2. It lacks selectivity and in applications where this is a preference, energy requirements are further increased.
3. It has a higher solubility in liquid hydrocarbon streams than many other amines.
4. Corrosion potential limits solution strength to about 15% by weight.
5. A portion of the COS removed reacts irreversibly with the MEA causing losses.

When diethanolamine DEA is considered as a replacement for MEA, its advantages and disadvantages include some of the following:

Advantages

1. It has lower heats of reaction.
2. It has a slight selectivity for $H_2S$ over $CO_2$.
3. It is slightly less soluble in liquid hydrocarbons.
4. It can remove COS in some cases to acceptable levels.

Disadvantages

1. It has insufficient selectivity for tail gas treating.
2. Reclaiming is not a common, straight-forward process.
3. It forms irreversible products with $CO_2$ creating losses of the absorbent.
4. It doesn't produce treated gas specifications as low as MEA.

A refinery choosing methyldiethanolamine MDEA as a replacement for MEA and/or DEA does so based on the following advantages out-weighing the disadvantages:

Advantages

1. It has still lower heats of reaction than either MEA or DEA.
2. It has the required $H_2S$ to $CO_2$ selectivity required for tail gas treating and other gas streams containing $CO_2$ and $H_2S$.
3. It is slightly less soluble in liquid hydrocarbons.
4. It is more resistant to chemical degradation.
5. It is not corrosive.
6. Solution strengths up to 50% can be used for added acid gas removal capacity.

Disadvantages

1. It doesn't produce treated gas specifications as low as MEA or DEA.
2. It isn't known for its ability to remove COS.
3. Reclaiming is feasible but somewhat more difficult than MEA but not as complex as DEA.
4. Solvent cost is higher.

It would be advantageous to have a plant designed to remove all of these acid gases to the aforesaid levels producing a hydrocarbon product useful in the many latter processes. Such a designed acid gas treating plant liquid (liquified) and gas are indicated by the trade in the term gas treating plant is described consisting of a series of unit operations which integrate into the existing processes both from the mode of operation and the equipment which is used to produce commercially soluble products for polymerizations, combustions and the like.

BRIEF DESCRIPTION OF THE INVENTION

In accordance with the present invention a natural or synthetic gas stream or liquid (liquified) hydrocarbon stream as for example, a $C_3/C_4$ stream from a refinery debutanizer which contains acid gases such as $H_2S$, $CO_2$, COS (carbonyl sulfide), mercaptans (methyl, ethyl, propyl, butyl and even higher alkyl moieties) can be freed of these undesirable components by:

(1) Treatment of the gas or liquid stream with a formulated aqueous absorbent consisting of a selective $H_2S$ absorbent, e.g. methyldiethanolamine (MDEA) and a highly active COS absorbent/hydrolyzer, e.g. diisopropanolamine (DIPA) wherein the $H_2S$ is selectively absorbed and COS hydrolyzed to $H_2S$ and $CO_2$, the products being absorbed by the selective $H_2S$ absorbent in the desired selective range. The formulated absorbent is regenerated (stripped of $H_2S$) and returned to the absorber. Some make up of COS absorbent/hydrolyzer is necessary when liquid (liquified) hydrocarbons are treated because of solubility of these classes of compounds in the liquid hydrocarbons.

The so treated gas stream or liquid hydrocarbon will be found to have between 30 and 80 percent of the COS removed as compared with only 10-30 percent when a selective amine is used alone.

Further, by employing a selective $H_2S$ absorbent at this stage of the process the $H_2S$ to $CO_2$ ratio picked up by the absorbent can be adjusted to provide a regenerator gas product suitable for economical operations of most commercial sulfur recovery processes, e.g. a Claus Unit. In addition, since the COS is partially converted to $H_2S$ and $CO_2$, later treatments to remove the other acid gases are able to produce less contaminated waste streams, many of which can be after-treated to useful products and the treating solutions regenerated to provide more economical operations. Substantially any of the secondary and/or tertiary alkanolamines can be employed in this step, each having a recognized advantage under the operating parameters of absorber operations, feed stream conditions and available battery utilities. The exemplary discussions employ methyldiethanolamine which based on the ratio of $H_2S$ and $CO_2$ in the feed stream provided a regenerator off-gas with an $H_2S$ to $CO_2$ ratio to fit an existing Claus Unit operating parameters in the refinery. Other sulful conversion processes, as well as a similar process on a different scale, may require other ratios of $H_2S$ to $CO_2$ which will dictate the selection of the selective absorbent. The selectivity of the various absorbents, particularly the amines and more particularly the secondary and tertiary alkanolamines are well documented in the literature and one can be found without undue experimentation to give the most effective use of existing equipment.

In addition, by using a selective $H_2S$ absorbent formulated to contain an organic liquid COS solvent (absorbent) the losses of both solvent absorbents is reduced since most selective $H_2S$ sorbents are less soluble in liquid (liquified) hydrocarbon streams and smaller quantities of the COS sorbent are possible thus reducing its losses.

(2) Treatment of the resulting product gas or product liquid (liquified) hydrocarbon stream with an aqueous formulated alkali (caustic)-primary alkanolamine solution wherein the contact time is such to remove 50-80 percent of the remaining COS but "slip" most of the mercaptans. The concentration of caustic is in the range of 5 to 50% by weight and the alkanolamine preferably a primary alkanolamine, in from about 0.5 to 20% by weight, the remainder of course being water. It has been found advantageous to employ a single stage contactor. The COS being converted herein to $Na_2S$ and $Na_2CO_3$, which mixture may be used to generate $S°$ and $CO_2$ or used per se in several industrial processes, e.g. paper production.

(3) The gas or liquid stream from the 2nd step is then contacted with a 5 to 50 and preferably a 10-25 percent by weight of an unformulated aqueous alkali solution (NaOH) in a "structured" packed zone of several stages, preferably a minimum of six stages. Here essentially all of the mercaptans are removed as well as an additional 70-90 plus percent of the remaining COS. The waste stream from this treatment may be regenerated in known manners.

(4) Following these treatments the hydrocarbon stream, if liquid, is washed with water to remove residual alkali, and again, if a liquid stream as for example from a debutanizer, is further split into its components, e.g. $C_3$ and $C_4$ and the $C_3$ or the product gas, if from a natural or synthetic source, is "polished" substantially free of COS, which of course goes with the lower boiling components ($C_3$) or remains in the gas streams, by contacting it with a final formulated aqueous alkali/alkanol amine solution in a structured multi stage contactor.

The product is finally washed to remove any traces of alkali or alkanolamine and is found to be substantially free of sulfur containing organic and inorganic acid gases, COS in the range of less than 1000 ppb and usually less than about 100 ppb.

It is of course to be understood that any of the above steps may be eliminated, bypassed or included, with greater or reduced contact times, recirculation rates and/or strength $H_2S$ if more sulfur removal is required or less sulfur removal is acceptable.

The formulated solutions employed in accordance with the present invention are of two general scopes:

(a) an aqueous solution of (i) a selective hydrogen sulfide absorbent such as methyldiethanolamine, and (ii) a COS absorbent/hydrolyzer under the conditions of selective $H_2S$ absorbtion such as diisopropanolamine; and, (b) an aqueous solution of an alkali metal hydroxide containing various amounts of at least one alkanolamine.

In addition it is advantageous to employ "structured" packing having a high surface-to-volume ratio, such as Goodloe knitted packing, in the formulated alkali/alkanolamine treatment steps.

The percent removal of each component is related to the strength of the treating solutions, the contact time, and the loadings are dependent on the circulation rates.

The first step treatment, the combined primary $H_2S$ removal step and COS initial hydrolysis step, is carried out in a multi stage contactor or absorber designed to provide a contact time of the gas or liquid (liquified) hydrocarbons with the formulated $H_2S/COS$ absorbent-hydrolysis solution of from about 50 to 120 seconds. Such contact times give enhanced COS removal, maximize the selective removal of $H_2S$ vis-a-vis $CO_2$, minimize solubility of the COS hydrolyzer in liquid hydrocarbon and yet permit $H_2S$ loading of about 0.2 moles $H_2S$ per mole of selective $H_2S$ absorbent.

Temperature of the selective $H_2S$ absorbent/COS absorbent-hydrolysis contact should be in the range of 40° to 90° C.

The temperature of the alkali treatments, both formulated and unformulated, ranges from about 40° to 70° C.

The concentration of the components of the various formulations is as follows:

(a) aqueous formulated $H_2S/COS$ absorbent-hydrolysis solutions of from 5 to about 60% by weight are operable but, preferably these solutions contain 20% to 50% by weight of the $H_2S$ absorbent and from about 0.5 to about 15% by weight and preferably from about 1% to about 10% of the COS absorbent hydrolyzer.

(b) aqueous formulated alkali/alkanolamine solutions contain 5 to 50% and preferably contain 5% to 25% of the alkali metal hydroxide and 0.5 to 20% and preferably 2% to 15% of the primary alkanolamine;

(c) the aqueous unformulated alkali scrubber solution contains 5 to 50% by weight and preferably 10% to 25% alkali metal hydroxide.

The loading of the $H_2S$ absorber/COS absorber-hydrolyzer solution is generally held below about 0.25 moles $H_2S$ per mole absorbent and preferably at about 0.2 moles per mole.

The scope of selective $H_2S$ absorbents operable in accordance with the present invention is as wide as the known art but for energy conservation, a selective absorbent, a tertiary amine such as methyldiethanolamine or diethylethanolamine is preferred, since total heat duty is about ½ that of, for example, MEA at 20% concentrations. Other selective alkanolamine absorbents are well documented relative to heat duty and can be selected on the basis of each installation design, available heating and cooling sources outside the battery of the present invention, and selectively of pick-up.

BRIEF DESCRIPTION OF THE DRAWING

The sole FIGURE illustrates the sulfur removal process of the present invention and concentration levels of selected process streams.

DETAILED DESCRIPTION OF THE INVENTION

Figures 1, 2:
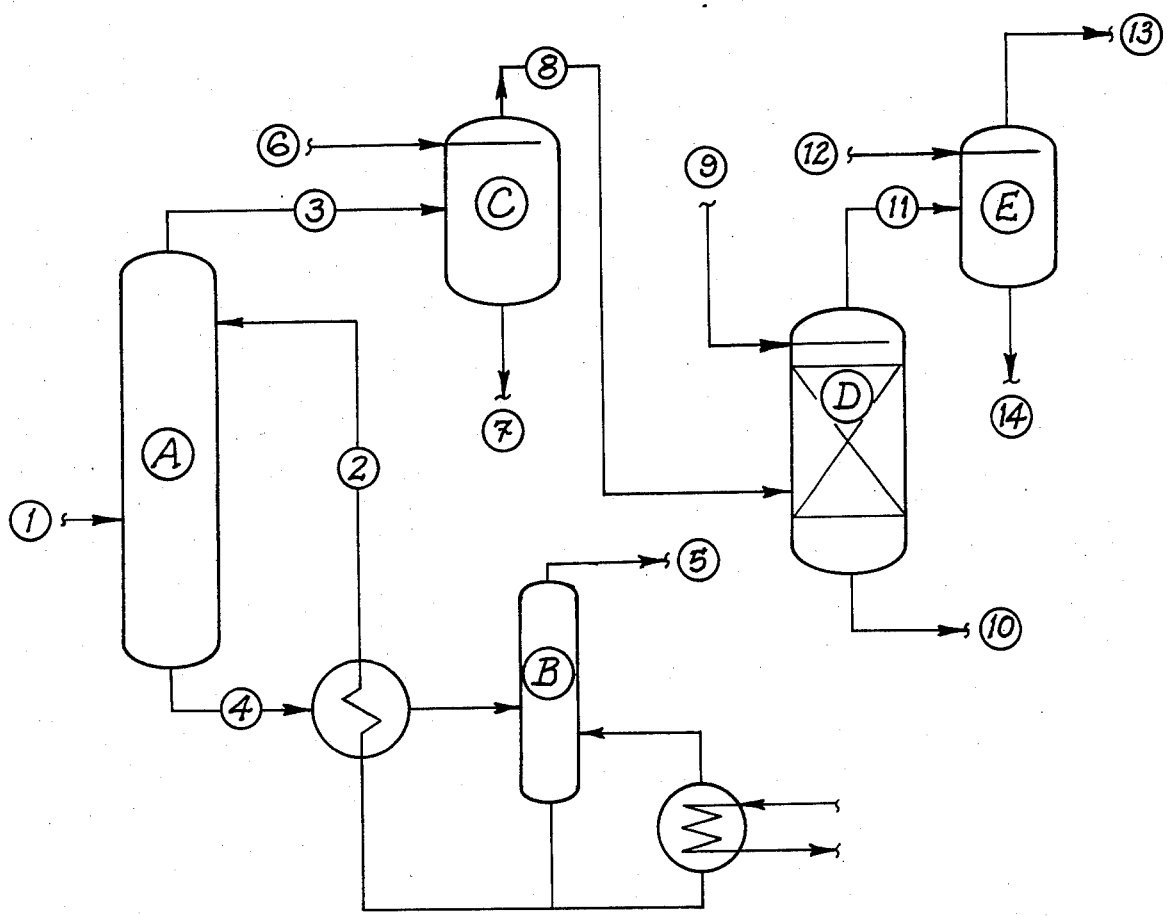

In a representative example with specific reference to the drawing which is a schematic of a portion of a light hydrocarbon processing plant of a refinery FIG. 1, a natural or snythetic gas stream or a liquid or liquified petroleum hydrocarbon stream (1) was fed to a multi-stage absorber (A) of conventional design to employ an alkanolamine to remove acid gases. In the representative example the original absorbent was monoethanolamine (MEA). The absorbent stream (2) in accordance with the present invention was a lean formulated selective $H_2S$ alkanolamine absorbent (methyldiethanolamine containing diisopropanolamine) which replaced the MEA absorbent previously used. The rich sorbent (4) was withdrawn from the bottom of the absorber and contained the absorbents, $H_2S$ and $CO_2$ tied-up in the absorbent. A major portion of the COS had been hydrolyzed to $H_2S$ and $CO_2$ which were of course picked-up by the sorbents in their selective ratios. The rich absorbent (4) was regenerated in a stripper (B), the resulting hot lean sorbent cooled by cross exchange with the cold rich stream (4), and the lean stream (2) returned to the absorber (A). The off-gas from the stippper, stream (5) contained $H_2S$ and $CO_2$ in a ratio which was suitable for sulfur recovery in for example a Claus sulfur unit. The hydrocarbon stream exiting the absorber, stream (3) contained very little $H_2S$, the "slipped" $CO_2$, the mercaptans and still contained from 70-20 percent of the COS that had been in the incoming hydrocarbon stream (1).

The treated hydrocarbon is sent to a single stage contactor (C) where it is connected with formulated caustic solution (aqueous sodium hydroxide) containing monoethanolamine stream (6). The flow rates are adjusted to provide a pick up of above 50 to 80 percent of the remaining COS and most of the $CO_2$ (COS+NaOH→$Na_2S$+$Na_2CO_3$) and "slip" a major portion of the mercaptans. The hydrocarbon stream (8) now contains only traces (ppm) of $H_2S$, and $CO_2$, the major portion of the mercaptans and some residual COS.

This stream, stream (8) was treated with an aqueous caustic solution over a structured packing, e.g. Goodloe woven mesh in column D. Here, the intimate multi-stage contact of the stream with the caustic permits the mercaptans to be converted to their salt form and pass downwardly with the aqueous caustic treating solution while the hydrocarbons pass upwardly and out of the treater.

At this point the major sulfur containing compounds (acid gases) have been removed and in many cases the residual of these gases remaining is insignificant and the hydrocarbons can be used directly in downstream processes. However, should lower level acid gas contents be required the, hydrocarbon stream can be polished to remove the acid gases particularily the COS to parts per billion by a subsequent treatment with a formulated aqueous caustic solution in a contactor packed with a structured packing. For example in the liquid hydrocarbon section of the refinery it is customary to fractionate the treated streams of mixed hydrocarbons and if such is the design it will be obvious that the COS and most other acid gases will go with the lighter fractions of the hydrocarbons. Such treatment will increase the concentration of the acid gases in the light end, in the case of the refinery treating a debutanizer stream, or mixture of $C_3$'s and $C_4$'s, the concentration of COS will about double in the C overhead, and if this stream is to be used in the polymerization reactions, must be again treated to remove the COS to less than 50 ppb. By following the steps as herein set forth, COS and total sulfur in hydrocarbon streams can be reduced to less than 50 ppb.

The following data illustrates the significant improvement in acid gas removal from the light hydrocarbons processing streams of one refinery.

A refinery debutanizer product was employed which consist mainly of $C_3$ and $C_4$ liquified petroleum gases containing $H_2S$, COS and mercaptans ($C_{1-4+}$). This section of the plant was operated using MEA, then MDEA and finally formulated MDEA with the formulated alkali in accordance with the present invention. The following table documents the results using the various formulated solutions of the present invention compared to the original solutions starting with MEA, changing MEA to MDEA then the formulated MDEA solutions; Example A is projected from experience based on Example 3 using higher concentrations of MDEA and 2% DIPA.

| Case Number | 1 | 2 | 3 | 4 |
|---|---|---|---|---|
| Solvent | MEA | MDEA | MDEA[1] | MDEA[1] |
| Conc. wt % | 15 | 20 | 20 | 50 |
| Circ. rate gpm | 1179 | 1179 | 1179 | 462 |
| X-Exch. Approach temp °F. | 30 | 30 | 30 | 30 |
| Reflux H$_2$O/acid gas | 1.2 | 1.2 | 1.2 | 1.2 |
| Heat of Reaction Calc. MMBTUH | 7419 | 4304 | 4304 | 4304 |
| Reflux Latent Heat MMBTUH | 6218 | 5561 | 5561 | 5561 |
| Sensible Heat MMBTUH | 17292 | 16989 | 16989 | 6516 |
| Reboiler duty MMBTUH | 30929 | 51204 | 26854 | 16381 |
| COS before contactor (ppm) | | 3 | 3 | 3 |
| after contactor (ppm) | | 2 | 1 | 1 |
| after caustic scrubber (ppm) | | 2[2] | 0.05–0.1[3] | 0.05–0.1[3] |

[1]formulated with ca 2% DIPA
[2]15% NaOH
[3]15% formulated NaOH

In another example a synthetic gas stream containing 3.5 volume percent H$_2$S, 500 ppm COS, 2500 ppm each of methyl and ethyl mercaptan was feed at 50° C. and 50 psig for COS removal through a high surface area to volume structured packing (Goodloe unit packing) at various liquid to gas ratios (L/G) and temperatures to obtain the effect of L/G and temperature on COS removal in the presence of RSH (mercaptans) and H$_2$S by a 10% sodium hydroxide, 90% water solution. The results are listed below as well as a single stage contactor results which illustrates the benefit of the inclusion of such a unit operation in the preferred embodiment of the present invention.

TABLE 1

Caustic Removal of H$_2$S, COS, EtSH, and MeSH

| Solution | L/G | Temp. | % Removal of Acid Gases | | | |
|---|---|---|---|---|---|---|
| | | | COS | H$_2$S | EtSH | MeSH |
| 10% NaOH and 90% Water Solution | .012 | 50° C. | 70 | 99.9 | 99.0 | 99.0 |
| | .012 | 55° C. | 80 | 99.9 | 99.2 | 99.2 |
| | .012 | 60° C. | 92 | 99.9 | 99.4 | 99.4 |
| | .016 | 50° C. | 70 | 99.9 | 99.0 | 99.4 |
| | .03 | 50° C. | — | 99.9 | 99.5 | 99.5 |
| | .03 | 50° C. | — | 99.9 | 99.5 | 99.5 |
| | .034 | 50° C. | — | 99.9 | 99.6 | 99.6 |
| | .034 | 50° C. | — | 99.9 | 99.9 | 99.9 |
| | .035 | 50° C. | — | 99.9 | 99.6 | 99.6 |
| | .041 | 50° C. | 68 | 99.9 | 99.6 | 99.7 |
| | .043 | 94° C. | 90 | 99.9 | 99.6 | 99.8 |
| | .046 | 50° C. | 80 | 99.9 | 99.9 | 99.9 |
| | .047 | 50° C. | 80 | 99.9 | 99.8 | 99.9 |
| | .047 | 85° C. | 94 | 99.9 | 99.7 | 99.8 |
| | .053 | 50° C. | 90 | 99.9 | 99.6 | 99.6 |
| | .053 | 50° C. | 66 | 99.9 | 99.6 | 99.6 |
| | .058 | 85° C. | 78 | 99.9 | 99.7 | 99.8 |
| | .064 | 50° C. | 82 | 99.9 | 99.8 | 99.9 |
| | .064 | 85° C. | 94 | 99.9 | 99.7 | 99.8 |
| | .069 | 50° C. | 82 | 99.9 | 99.9 | 99.9 |
| | .079 | 50° C. | 80 | 99.9 | 99.7 | 99.8 |
| No packing in column same solution | .012 | 50° C. | 0 | 95.7 | 89.2 | 91.9 |

0 indicates 0% removed
— indicates that the component was present but was not analyzed.

What is claimed is:

1. A method for treating liquid and gaseous hydrocarbon streams containing H$_2$S, CO$_2$ and COS to remove a substantial portion of said H$_2$S and COS, and slip a substantial portion of the CO$_2$ which comprises: contacting said hydrocarbon stream containing H$_2$S, CO$_2$ and COS with a solution of methyldiethanolamine, which is a selective absorbent for H$_2$S with respect to CO$_2$, and which solution also contains diisopropanolamine, an organic liquid COS absorbent which absorbent converts by hydrolysis the COS to H$_2$S and CO$_2$.

2. The method of claim 1 wherein the concentration of the alkanolamine is from about 5 to about 60% and the concentration of the COS absorbent is from 0.5 to about 15%, each based on the total weight of the composition, the balance being water.

3. A method for treating liquid and gaseous hydrocarbon streams containing H$_2$S, CO$_2$, and COS to remove a substantial portion of said COS and substantially all of said H$_2$S and CO$_2$, which comprises:
   (a) contacting said hydrocarbon stream, gas or liquid, containing H$_2$S, CO$_2$ and COS with an alkanolamine solution, methyldiethanolamine, which is a selective absorbent for H$_2$S with respect to CO$_2$ and which solution also contains an organic liquid COS absorbent, diisopropanolamine, which absorbent converts by hydrolysis the COS to H$_2$S and CO$_2$; and, thereafter,
   (b) treating the resulting hydrocarbon stream by contacting the stream with an aqueous caustic solution containing as the sole additional component a primary alkanolamine therby to remove from 50 to 80% of the COS remaining in the first treated hydrocarbon stream while slipping mercatans if present.

4. The method of claim 3 wherein the concentration of the alkanolamine absorbent is from about 5 to about 60% and the concentration of the COS absorbent is from 0.5 to about 15%, each based on the total weight of the composition, the balance being water.

5. The method of claim 3 wherein the primary alkanolamine of step (b) is monoethanolamine and is present in from about 0.5 to about 20% by weight and the caustic is present in from about 5 to about 50% by weight, the balance being water.

6. A method for treating liquid and gaseous hydrocarbon streams containing H$_2$S, CO$_2$, and COS to remove a substantial portion of said COS and substantially all of said H$_2$S, and CO$_2$, which comprises:
   (a) contacting said hydrocarbon stream, gas or liquid, containing H$_2$S, CO$_2$ and COS with an alkanolamine solution, methyldiethanolamine, which is a selective absorbent for H$_2$S with respect to CO$_2$ and which solution also contains an organic liquid COS absorbent, diisopropanolamine, which absorbent converts by hydrolysis the COS to H$_2$S and CO$_2$;
   (b) treating the resulting hydrocarbon stream by contacting the stream with an aqueous caustic solution containing as the sole additional component a primary alkanolamine thereby to remove from 50 to 80% of the COS remaining in the first treated hydrocarbon stream while slipping mercatans if present, and thereafter,
   (c) contacting the so treated hydrocarbon stream with an aqueous caustic solution in a multi-stage contactor.

7. The method of claim 6 wherein the concentration of the alkanolamine is in from about 5 to about 60% and the concentration of the COS absorbent is from 0.5 to about 15%, each based on the total weight of the composition, the balance being water.

8. The method of claim 6 wherein each caustic solution is from about a 5 to about a 50% by weight aqueous solution, the primary alkanolamine the sole additional component of the caustic solution of step (c) is monoethanolamine and is present in from about 0.5 to about 20% by weight.

9. A method for treating liquified petroleum hydrocarbon streams containing acid gases, including COS, $H_2S$, $CO_2$, and mercaptans, to remove a substantial portion of said acid gases, which comprises:
   (a) contacting said hydrocarbon stream containing $H_2S$, $CO_2$ mercaptans and COS, with an alkanolamine absorbent solution which absorbent is a selective absorbent for $H_2S$ with respect to $CO_2$ and which solution also contains an organic liquid COS absorbent which absorbent converts by hydrolysis the COS to $H_2S$ and $CO_2$,
   (b) contacting the so treated stream with a caustic solution containing as the sole additional component a primary alkanolamine,
   (c) contacting the so treated stream with an aqueous caustic solution in a multi-stage contactor,
   (d) treating the so treated stream in a C3/C4 splitter, and, thereafter,
   (e) treating at least a portion of the lights overhead from said splitter with a caustic solution containing a primary alkanolamine, in a multi-stage contactor.

10. The method of claim 9 wherein the selective alkanolamine absorbent of step (a) and the said COS absorbent are present as an aqueous solution.

11. A method for treating liquified petroleum hydrocarbon streams containing acid gases, including COS, $H_2S$, $CO_2$, and mercaptans, to remove a substantial portion of said acid gases, which comprises:
   (a) contacting said hydrocarbon stream containing $H_2S$, $CO_2$, mercaptans and COS, with a seelective alkanolamine absorbent solution, methyldiethanolamine, which absorbent is a selective absorbent for $H_2S$ with respect to $CO_2$ and which solution also contains an organic liquid COS absorbent diisopropanolamine which absorbent converts by hydrolysis the COS to $H_2S$ and $CO_2$,
   (b) contacting the so treated stream with a caustic solution containing as the sole additional component a primary alkanolamine,
   (c) contacting the so treated stream with an aqueous caustic solution in a multi-stage contactor,
   (d) treating the so treated stream in a C3/C4 splitter, and, thereafter,
   (e) treating at least a portion of the lights overhead from said splitter with a caustic solution containing a primary alkanolamine, in a multi-stage contactor.

12. The method of claim 11 wherein the concentration of the alkanolamine is from about 5 to about 60 and the concentration of the COS absorbent is from 0.5 to about 15%, each based on the total weight of the composition, the balance being water.

13. The method of claim 11 wherein the primary alkanolamine of steps (b) and (e) is monoethanolamine and is the sole additional component in such solutions and is present in from about 0.5 to about 20% by weight and the caustic concentration of each of said caustic solutions of steps (c) and (e) is from about 5 to about 50% by weight.

* * * * *